United States Patent [19]

Irvin et al.

[11] 4,177,250
[45] Dec. 4, 1979

[54] METHOD OF REMOVING ACETYLENE AND SULFUR COMPOUNDS FROM GASES BY ABSORPTION IN DIMETHYL FORMAMIDE

[75] Inventors: Howard B. Irvin; Fred T. Sherk; Alfred A. Hoffman, Jr., all of Bartlesville, Okla.

[73] Assignee: Phillips Petroleum Company, Bartlesville, Okla.

[21] Appl. No.: 843,198

[22] Filed: Oct. 18, 1977

Related U.S. Application Data

[62] Division of Ser. No. 714,934, Aug. 16, 1976, Pat. No. 4,086,288.

[51] Int. Cl.$^2$ .................. B01D 53/34; C01B 17/04
[52] U.S. Cl. .................. 423/573 G; 423/226; 423/245; 55/64; 55/73; 585/448; 585/717; 585/862; 585/910
[58] Field of Search .............. 423/220, 222, 224, 226, 423/245, 573 G, 573 R; 260/677 A, 683.49, 683.53, 683.43, 671 R; 55/63–65, 73

[56] References Cited

U.S. PATENT DOCUMENTS

| | | | |
|---|---|---|---|
| 2,251,216 | 7/1941 | Woodhouse | 55/73 |
| 2,970,177 | 1/1961 | Cobb, Jr. | 260/683.49 X |
| 3,530,199 | 9/1970 | Lowrance | 55/64 X |

FOREIGN PATENT DOCUMENTS 1091995  4/1961  Fed. Rep. of Germany ....... 423/573 L

*Primary Examiner*—Earl C. Thomas

[57] ABSTRACT

Dimethyl formamide when used as an absorption solvent to remove acetylenes from olefin-containing gas streams acts as well as a promoter for the oxidative conversion of $H_2S$, COS, and/or $CS_2$, also contained in the feed stream, to elemental sulfur. Thus both acetylenes and sulfur compounds are efficiently removed from such olefin-containing gas streams as coke oven gas. Further, the loss of dimethyl formamide entrained and vaporized by the deacetylenized gas stream leaving the dimethyl formamide absorber is substantially reduced or effectively eliminated by the injection of a stream of liquid selected from the group consisting of paraffinic hydrocarbons having 4–8 carbon atoms per molecule containing at least one tertiary carbon atom per molecule and aromatic hydrocarbons having 6–10 carbon atoms per molecule above the point of injection of the dimethyl formamide solvent stream to the absorption column. This liquid stream injection is particularly advantageous when the stream is also a reactant in a downstream alkylation process.

8 Claims, 1 Drawing Figure

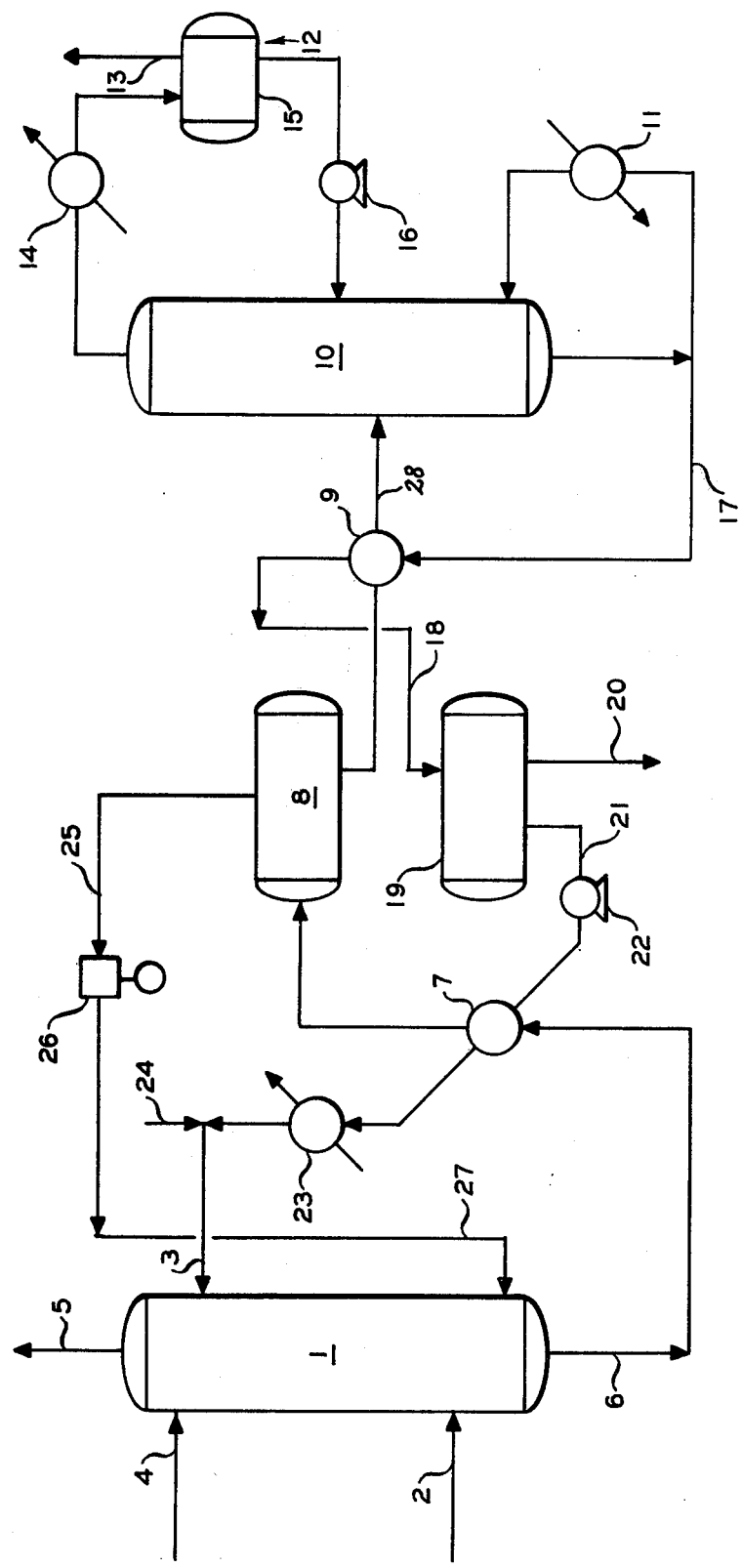

METHOD OF REMOVING ACETYLENE AND SULFUR COMPOUNDS FROM GASES BY ABSORPTION IN DIMETHYL FORMAMIDE

This application is a division of our copending application having Ser. No. 714,934, filed Aug. 16, 1976 now U.S. Pat. No. 4,086,288, entitled "Acetylenes Removal by Dimethyl Formamide Absorption."

This invention relates to the hydrocarbon separation. In one aspect, this invention relates to the removal of acetylenes from gas streams containing acetylenes and olefins.

In another aspect, this invention relates to the desulfurization of gas streams containing acetylenes, olefins, and sulfur compounds.

BACKGROUND OF THE INVENTION

It is well known in the art that N,N-dimethyl formamide (DMF) is an efficient selective solvent to remove, e.g., acetylenes, from gas streams containing such acetylenes in addition to olefins. One of the problems occurring in such an absorption process is that a small portion of the dimethyl formamide leaves the absorption zone overhead together with the deacetylenized gas. It already has been proposed to remove entrained selective solvent by contacting the absorber overhead gas stream raffinate with liquid ethylene. This procedure, generally applied to the removal of acetylene ($C_2H_2$) from ethylene ($C_2H_4$), when can basically be characterized as refluxing the absorption column with liquefied ethylene overhead gas, is fairly complicated and expensive because ethylene must be first liquefied and fed to the column with precise control to prevent substantial loss in the rich DMF kettle product from which the acetylenes are later stripped. If a separate contacting unit is utilized, as has been proposed in the art, the ethylene/dimethyl formamide mixture must later be separated so that a plurality of units is then required, which adds to the overall cost of the process and may render it economically unattractive.

It would thus be desirable to have a process available by which the expensive dimethyl formamide solvent leaving the dimethyl formamide absorber overhead with the product gas is readily and relatively inexpensively recovered.

Furthermore, it is known in the prior art that such commercially available gas streams as coke oven gas contain sulfur compounds such as $H_2S$, COS, and $CS_2$. These low-boiling sulfur compounds are very undesirable and need to be removed to prepare suitable feedstock for processes utilizing such gases. Thus it would be desirable to have a process available by which the sulfur compounds in gases such as coke oven gas can be readily removed as well.

THE INVENTION

It is thus one object of this invention to provide a new process for extracting or absorbing acetylenes from gas streams containing acetylenes and olefins.

Another object of this invention is to provide a process for the absorption of acetylenes from gases containing acetylenes and olefins essentially without removal of dimethyl formamide overhead with the deacetylenized gas stream.

Furthermore, it is an object of this invention to provide a solvent absorption process utilizing dimethyl formamide as the solvent and in which essentially no dimethyl formamide is lost.

Yet another object of this invention is to provide a process for the desulfurization of coke oven gas containing oxidizable sulfur compounds such as $H_2S$, COS, $CS_2$, and free oxygen.

Still a further object of this invention is to provide a process for desulfurizing and deacetylenizing coke oven gas containing sulfur compounds comprising $H_2S$, COS, $CS_2$, and free oxygen, olefins, and acetylenes.

These and other objects, advantages, details, features, and embodiments of the present invention will become apparent to those skilled in the art from the following detailed description of the invention, the examples, the appended claims, and the drawing which shows a schematic flow diagram of a deacetylenizing and desulfurizing unit for coke oven gas.

In accordance with one aspect of this invention, we have now found that a gas containing olefins, acetylenes, oxygen, and one or more oxidizable sulfur compounds, e.g., selected from the group consisting of $H_2S$, COS, and $CS_2$, can be both effectively deacetylenized and desulfurized by contacting this gas with liquid N,N-dimethyl formamide.

The liquid N,N-dimethyl formamide absorbs or extracts the acetylenes, whereas the sulfur compounds are converted or oxidized to elemental sulfur. This absorption and reaction process preferably is carried out in the presence of a small quantity of water, e.g., 0.01 to 1.00 part by weight of water per 100 parts by weight of pure dimethyl formamide. An absorber kettle product stream, comprising a liquid phase of dimethyl formamide with dissolved acetylenes, and a minor second phase of solid or liquid elemental sulfur (depending upon temperature) is formed. This rich solvent stream is later readily separated into an acetylene gas stream, a liquid dimethyl formamide solvent stream for recycle to the dimethyl formamide absorber, and a liquid sulfur stream by heat stripping.

The liquid effluent from the dimethyl formamide absorber, in which the acetylenes are selectively dissolved in the liquid dimethyl formamide from a feed gas comprising acetylenes and olefins, can be passed to a flash tank wherein, by means of heat exchange and pressure reduction, a gas stream can be flash-vaporized from the rich solvent comprising principally olefins (butylenes, propylene, and ethylene) with some acetylene and methyl acetylene included. This gas stream can be recompressed and injected as stripping gas into the lower portion of the absorption column. The partially stripped or denuded solvent is passed to the DMF stripper or deacetylenizer, wherein the acetylenes are distilled off and removed as an overhead gas, and the stripped, liquid dimethyl formamide stream, in which a minor amount of a separate liquid sulfur phase is dispersed, is removed from the bottom of the stripper. The two liquid phases can be separated in a settler after cooling as desired, and essentially sulfur-free dimethyl formamide is withdrawn from this settler and recycled to the dimethyl formamide absorbing unit. Liquid sulfur is also withdrawn from this settler as the heavy liquid phase.

The gas that is deacetylenized and simultaneously desulfurized in the dimethyl formamide absorber generally comprises major portions of methane, hydrogen, ethylene, and other olefins being the components of interest, and containing contaminants such as acetylene, methyl acetylene, and one or more sulfur compounds such as $H_2S$, COS, and/or $CS_2$. The gas usually further contains carbon oxides and some free oxygen; alternatively a small amount of oxygen can be added to provide same, e.g., by adding some air. The exact composition of the gas treated in accordance with this invention is not critical except for the presence of acetylenic compounds and oxidizable sulfur compounds as contaminants to compounds of economic significance.

The preferred gas treated in accordance with this invention is coke oven gas. This gas is produced by the old and well-known process of coking or carbonizing coals wherein considerable volumes of gas are generated both by decomposition and partial oxidation. Processes and gases generated therefrom are widely described such as in the Encyclopedia of Chemical Technology, Kirk-Othmer, Volume 4, pages 400–423, particularly 415–416.

In accordance with another aspect of this invention, we have discovered that entrained dimethyl formamide, utilized as an absorption solution in an acetylene gas absorption or treating process, can be readily recovered from absorber overhead deacetylenized gas if a liquid stream selected from the group consisting of paraffinic hydrocarbons having 4–8 carbon atoms per molecule containing at least one tertiary carbon atom, and aromatic hydrocarbons having 6–10 carbon atoms per molecule, is injected into the absorber above the location of injection of the liquid dimethyl formamide. A particularly preferred variation of this embodiment of the invention consists in utilizing the above-described absorption process in combination with an alkylation process. In this combined process, a gas stream containing at least one olefin and at least one acetylene is contacted with dimethyl formamide. The stream of non-absorbed gas comprising olefin (alkylatable material) is utilized in an alkylation step, together with an alkylant (alkylating agent) such as to produce an alkylate. A portion of the alkylant is also injected into the dimethyl formamide absorber above the location of injection of liquid dimethyl formamide such as to "wash down" the dimethyl formamide that may be vaporized and/or entrained into the overhead olefin-containing gas stream. The alkylant that is contained in the overhead gas stream leaving the dimethyl formamide absorber does not have to be separated from this gas stream because this alkylant is also a feed material to the downstream alkylation reaction. In this alkylation reaction the olefin and the alkylant are reacted to form an alkylate in the presence of a catalyst. Alkylation processes as such are well known in the art. Examples of such alkylation processes are the alkylation of ethylene, propylene, and/or butylene with isobutane or isopentane in the presence of, e.g., an HF catalyst, and the alkylation of ethylene with benzene in the presence of an aluminum halide or hydrofluoric acid catalyst.

The olefin plus isoparaffin alkylation process results in high-octane alkylates useful as premium motor fuel components. The ethylene plus aromatics alkylation process results in such products as ethylbenzene (useful as an intermediate to make styrene-polystyrene), cumene (useful as a fuel additive), and diethylbenzene (useful as an intermediate to make divinylbenzene and polymers incorporating it). In the first-mentioned alkylation process, the isoparaffin is injected to wash down the dimethyl formamide whereas the aromatic hydrocarbon is used for this purpose if the purified olefin stream is used in the second type of alkylation (with an aromatic hydrocarbon).

In the preferred embodiment of this invention in which coke oven gas is deacetylenized by contacting the coke oven gas with dimethyl formamide, the liquid hydrocarbon that is injected above the location of dimethyl formamide injection into the absorber is benzene. The overhead gas leaving the dimethyl formamide absorber contains ethylene and benzene, and this gas is passed to an alkylation unit in which ethylbenzene is produced. Processes for converting ethylene and benzene to ethylbenzene are described in more detail, e.g., in U.S. Pat. Nos. 3,123,650; 2,372,320; and 2,456,435.

The most preferred embodiment of this invention combines both the desulfurization, the acetylene removal from the gas, and the dimethyl formamide removal from the raffinate gas as described above. Thus in accordance with the most preferred embodiment of this invention, a gas comprising an olefin, oxygen, and, as contaminants, acetylenes and one or more oxidizable sulfur compounds, e.g., those selected from the group consisting of $H_2S$, COS, $CS_2$, is contacted in an absorber with liquid dimethyl formamide, such as to remove the acetylenes from this gas and at the same time to convert the sulfur compounds into elemental sulfur. Above the locus of injection of the liquid dimethyl formamide, a hydrocarbon liquid stream, as defined above, is injected such as to remove substantially all of the dimethyl formamide contained in the deacetylenized and desulfurized gas stream. The liquid bottoms effluent from the DMF absorber is separated into a gas stream comprising acetylene, a first liquid stream consisting of essentially pure dimethyl formamide and a second liquid stream consisting essentially of sulfur. The gaseous overhead stream leaving the absorber comprises the olefin as well as a portion of the liquid hydrocarbon stream injected. This liquid hydrocarbon stream, in accordance with this preferred embodiment of the invention, constitutes at least a portion of the alkylant with which the olefin is reacted in a downstream alkylation process.

Further details and preferred embodiments will become apparent to those skilled in the art from the following description of the drawing, which shows a schematic diagram for the removal of impurities by absorption in dimethyl formamide from coke oven gas.

Into a dimethyl formamide absorber 1, a coke oven gas stream is introduced via line 2. This coke oven gas stream is contacted with liquid dimethyl formamide introduced via line 3 into the upper portion of the dimethyl formamide absorber 1. Above the locus of injection of the dimethyl formamide into the absorber 1, a stream of liquid benzene is introduced via line 4. This stream of liquid benzene effectively washes out all of the entrained and/or vaporized dimethyl formamide contained in the non-absorbed upflowing gas stream, returning it to the bulk of the dimethyl formamide in liquid form. The non-absorbed gaseous stream, having the acetylenes and entrained dimethyl formamide removed, leaves the dimethyl formamide absorber 1 via line 5 overhead. This stream is commonly known as residue gas, but is more properly referred to here as the purified olefin-containing stream. A portion of the benzene is vaporized into this stream, and it may be said that this benzene takes the place of the vaporized dimethyl formamide by virtue of the relative vapor pressures. Within absorber 1, in contact with liquid dimethyl formamide, low concentrations of sulfur compounds are substantially oxidized by the low concentration of oxygen in the coke oven gas feed to form elemental sulfur and water from $H_2S$ (or carbon dioxide from COS and $CS_2$), the sulfur appearing as a highly dispersed second phase in the dimethyl formamide.

The liquid effluent leaving the dimethyl formamide absorber 1 via line 6 as bottoms-enriched solvent consists essentially of two phases, namely, the dimethyl formamide having dissolved therein the extracted acetylenes and sulfur present either as liquid or dispersed solids, depending upon temperature. This stream is passed via an indirect heat exchanger 7 to a flash tank 8. From this flash tank 8, a liquid stream 28 still containing the two phases of dimethyl formamide and sulfur is passed via a heat exchanger 9 to a stripper 10. From this stripper 10, equipped with a reboiler 11, as well as a reflux unit 12, a gaseous stream consisting essentially of acetylenes is withdrawn via line 13. The reflux unit 12 consists of a cooler-condenser 14, an accumulator vessel 15, and a reflux pump 16.

The liquid effluent from the stripper 10 is passed via line 17 through the indirect heat exchanger 9 and via line 18 to a hot liquid phase separation settler 19. From this settler 19 liquid sulfur is withdrawn via line 20 and liquid dimethyl formamide is withdrawn via line 21. This liquid dimethyl formamide is pumped by pump 22 through the heat exchanger 7 and a further cooler 23 to line 3 for reinjection into the dimethyl formamide absorber 1. Makeup dimethyl formamide to compensate for losses in the system and withdrawal for purification purposes (not shown) is added via line 24.

The gaseous effluent from the flash drum 8 is passed via line 25 and compressor 26 to line 27 via which this compressed gas is reinjected into the dimethyl formamide absorber 1 near the bottom thereof to increase the degree of acetylenes absorption and ethylene rejection by the DMF in absorber 1.

In the following, a typical calculated material balance is given for the system shown in the drawing. The quantities shown in this following table are kg/hr and the stream numbers are the same as those used in the drawing.

TABLE I

Material Balance Calculated for a Dimethyl Formamide Absorption System as Shown in the Drawing

| Stream No. | 2 | 4 | 3 | 5 | 28 | 13 | 17 | 20 | 24 |
|---|---|---|---|---|---|---|---|---|---|
| Component: | | | | | | | | | |
| $H_2$ | 739 | | | 739 | | | | | |
| $N_2$ | 1464 | | | 1464 | | | | | |
| $O_2$ | 319 | | | 237 | | | | | |
| CO | 1185 | | | 1185 | | | | | |
| $CO_2$ | 5338 | | | 4965 | 399 | 399 | | | |
| COS | 73 | | | — | 38 | 38 | | | |
| $H_2S$ | 169 | | | — | 15 | 15 | | | |
| $CH_4$ | 4243 | | | 4243 | — | — | | | |
| $C_2H_2$ | 194 | | | — | 194 | 104 | | | |
| $C_2H_4$ | 6345 | | | 6250 | 95 | 95 | | | |
| $C_2H_6$ | 2241 | | | 2241 | — | — | | | |
| $C_3H_4$ | 149 | | | — | 149 | 149 | | | |
| $C_3H_6$ | 575 | | | 480 | 95 | 95 | | | |
| $C_3H_8$ | 274 | | | 274 | — | — | | | |
| $C_4+$ | 1745 | | | — | 1745 | 1745 | | | |
| $C_6H_6$ | — | 84 | | 42 | 42 | 42 | | | |
| DMF | — | | 35860 | — | 35860 | 20 | 35840 | | 20 |
| $H_2O$ | — | | | — | 82 | 82 | | | |
| S | — | | | — | 163 | — | 163 | 163 | |
| TOTAL | 25053 | 84 | 35860 | 22120 | 38877 | 2874 | 36003 | 163 | 20 |

The operating conditions for the various units are exemplified in the following table by the temperatures and pressures of the streams, the compositions of which have just been shown:

TABLE II

| | Operating Conditions | |
|---|---|---|
| Stream No. | Temperature, °C. | Pressure, kPa, abs. |
| 2 | 27 | 2068 |
| 4 | 16 | 2068 |
| 3 | 16 | 2068 |
| 5 | 16 | 1993 |
| 28 | 90 | 1103 |
| 13 | 38 | 172 |
| 17 | 181 | 220 |
| 20 | 135 | 172 |
| 24 | 16 | 2068 |

Reasonable variations and modifications which will become apparent to those skilled in the art can be made in the present invention without departing from the spirit and scope thereof.

We claim:

1. A process for the simultaneous desulfurization of and acetylene removal from a gas which process comprises contacting a gas stream comprising an olefin and oxygen, and, as contaminants, acetylenes and at least one oxidizable sulfur compound selected from the group consisting of $H_2S$, COS, and $CS_2$, in an absorption zone with liquid dimethyl formamide such as to produce a gaseous effluent comprising the olefin and being essentially acetylene-free and a liquid effluent comprising dimethyl formamide, acetylenes, and sulfur, introducing a liquid hydrocarbon selected from the group consisting of paraffinic hydrocarbons having 4–8 carbon atoms per molecule, containing at least one tertiary carbon atom per molecule, and aromatic hydrocarbons having 6–10 carbon atoms per molecule into the absorption zone at a location above the location of introduction of said dimethyl formamide, and withdrawing a gaseous effluent stream from said absorption zone comprising said olefin and said hydrocarbon and being essentially acetylene and sulfur-free and introducing at least a portion of said gaseous effluent into an alkylation zone and reacting said olefin and said hydrocarbon in the presence of an alkylation catalyst to form an alkylate in said alkylation zone.

2. A process in accordance with claim 1 comprising separating said liquid effluent into a dimethyl formamide stream, an acetylene stream, and a sulfur stream.

3. A process in accordance with claim 1 comprising passing said liquid effluent to a separation zone in which said liquid effluent is separated into a gaseous stream comprising acetylenes and a liquid stream comprising dimethyl formamide and sulfur, passing said liquid stream to a settler and withdrawing a sulfur stream from said settler and withdrawing a dimethyl formamide stream from said settler.

4. A process in accordance with claim 2 wherein said dimethyl formamide stream is recycled into said absorption zone to absorb said acetylenes from said gas.

5. A process in accordance with claim 3 wherein said dimethyl formamide stream withdrawn from said settler is passed through indirect heat exchange relationship with said liquid effluent.

6. A process in accordance with claim 1 wherein said gas stream is a coke oven gas consisting essentially of hydrogen, nitrogen, oxygen, carbon monoxide, carbon dioxide, COS, $H_2S$, methane, acetylene, ethylene, ethane, methylacetylene, propylene, propane, and some heavier hydrocarbons.

7. A process for the simultaneous desulfurization of and acetylene removal from a gas which process comprises the steps of (a) contacting a gas stream comprising an olefin and oxygen, and, as contaminants, acetylenes and at least one oxidizable sulfur compound selected from the group consisting of $H_2S$, COS, and $CS_2$, in an absorption zone with liquid dimethyl formamide such as to remove the acetylenes from said gas and to convert the sulfur compounds into elemental sulfur, (b) injecting a liquid hydrocarbon selected from the group consisting of paraffinic hydrocarbons having 4–8 carbon atoms per molecule, containing at least one tertiary carbon atom per molecule, and aromatic hydrocarbons having 6–10 carbon atoms per molecule into an absorption zone at a location above the location of introduction of said dimethyl formamide, (c) separating the liquid bottoms effluent obtained from the absorber in step (a) into a gas stream comprising acetylene, a first liquid stream consisting essentially of pure dimethyl formamide and a second liquid stream consisting essentially of sulfur, and (d) passing the gaseous overhead stream obtained from the absorber in step (a), wherein said gaseous overhead stream comprises said olefin and a portion of the liquid hydrocarbon injected in step (b), to a downstream alkylation process.

8. A process in accordance with claim 1 wherein said liquid hydrocarbon is benzene and wherein said olefin is selected from the group consisting of ethylene, propylene and mixtures thereof.

* * * * *